United States Patent [19]

Albert

[11] 4,209,619
[45] Jun. 24, 1980

[54] HERBICIDAL COMPLEX AND FORMULATION

[75] Inventor: Robert E. Albert, Wilmington, Del.
[73] Assignee: E. I. Du Pont de Nemours and Company, Wilmington, Del.
[21] Appl. No.: 917,938
[22] Filed: Jun. 22, 1978
[51] Int. Cl.$^2$ ................ C07D 251/46; A01N 9/22
[52] U.S. Cl. ............................... 544/211; 71/93
[58] Field of Search .............................. 544/211

[56] References Cited
U.S. PATENT DOCUMENTS
3,902,887  9/1975  Lin .................................. 544/211

FOREIGN PATENT DOCUMENTS
2191845  2/1974  France .

OTHER PUBLICATIONS
Piskala. Chem. Abst. vol. 59 (1963) 10046h.
Gill et al. Chem. Abst. vol. 55 (1961) 24201i.
Nogam, et al. Chem. Abst. vol. 50 (1956) 2121d.

*Primary Examiner*—Catherine L. Mills

[57] ABSTRACT

A crystalline complex of 3-cyclohexyl-6-(dimethylamino)-1-(methyl)-s-triazine-2,4-(1H,3H)-dione and urea and improved herbicidal formulations thereof.

1 Claim, No Drawings

HERBICIDAL COMPLEX AND FORMULATION

BACKGROUND OF THE INVENTION

This invention relates to a herbicidal complex of 3-cyclohexyl-6-(dimethylamino)-1-methyl-s-triazine-2,4(1H,3H)-dione (hereinafter hexazinone) and urea in a molar ratio of 1:3.

3-Cyclohexyl-6-(dimethylamino)-1-methyl-s-triazine-2,4-(1H,3H)-dione (hereinafter hexazinone) is the active ingredient in Velpar ® herbicide products manufactured by E. I. du Pont de Nemours & Co., Inc., Wilmington, Del. 19898. While Velpar ® herbicide products can provide excellent control of a wide variety of weeds, brush and grasses at low application rates in industrial areas, i.e., rights-of-way, building foundations and the like, they are not generally suitable by themselves for agricultural uses.

It has been discovered that mixtures of hexazinone and 3-(3,4-dichlorophenyl)1,1-dimethylurea (hereinafter diuron) can provide good control of weeds and grasses in selected crops, particularly sugar cane. To avoid measuring errors, user exposure problems and delays which can occur when hexazinone and diuron formulations are tank mixed in the field just prior to use, it is often desirable that the two herbicides be formulated and sold as a mixture in a single package.

Field experience with hexazinone/diuron mixtures indicates that caking and agglomeration usually occur when the two herbicides are formulated as a wettable powder having more than about 60 percent by weight total active ingredients. The interaction of hexazinone and diuron appears to be a physical phenomenon which results in the formation of a eutectic composition which melts at about 60° C. The presence of this relatively low melting point eutectic hexazinone/diuron mixture can cause significant problems in blending, grinding and screening operations required to prepare wettable powder formulations, and it presents a serious limitation on active ingredient concentration, which, from a commercial standpoint, preferably should be about 70 to 95 percent by weight.

It has now been discovered that hexazinone and urea form a complex in a molar ratio of 1:3 which, when formulated with the hexazinone/diuron mixture as a wettable powder, prevents the eutectic hexazinone/diuron composition from forming, and permits hexazinone/diuron mixtures having greater than 60 percent by weight total active ingredients which are free from caking and agglomeration.

The prior art teaches that certain di- and triazine compounds can form complexes with urea. Coll. Czech, Chem. Commun., 28, 2376 (1963) (C.A. 59, 10046h), for example, discloses a 1:1 molar complex of urea and 1 a (or b) which can be formed by aqueous crystallization:

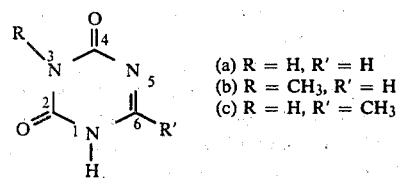

(a) R = H, R' = H
(b) R = CH₃, R' = H
(c) R = H, R' = CH₃

It is stated that urea adducts can be obtained from 5-azauracil (1a), 3-methyl-5-azauracil (1b), and 6-methyl-5-azauracil (1c). However, 1-methyl-5-azauracil and 4-methoxy-2-oxo-1,2-dihydro-1,3,5-triazine failed to form urea adducts. This would indicate that the hexazinone of this invention (2), i.e.,

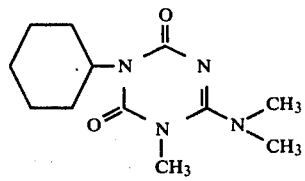

would not form a complex or adduct with urea.

The J. Phys. Chem., 65, 1432 (1961) (Ca. A. 55, 24201i) discloses the formation of a 2:1 molar complex of urea with piperazine 3 when

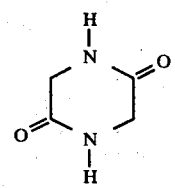

crystallized from an 8 molar aqueous urea solution.

Nippon Yakugakki Yakugaku Zasshi Tokyo, 75, 1029 (1955) (C.A. 50, 2121d) discloses that a 1:1 molar complex can be formed between urea and barbital 4, allobarbital 5, or ethylhexabital 6.

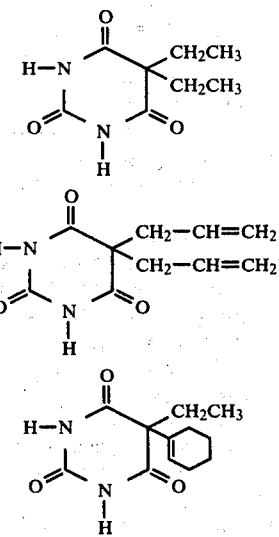

None of these references discloses a utility for any of the complexes which are taught.

SUMMARY OF THE INVENTION

It has been discovered that hexazinone and urea form a crystalline complex in a molar ratio of 1:3 which is a new chemical entity having a distinct melting point, a discrete crystalline habit and may be represented structurally by the following formula 7.

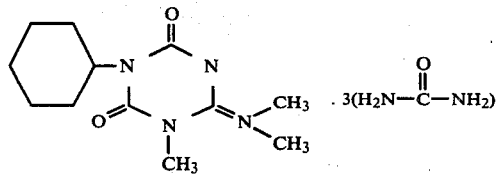

This invention also relates to a method of forming a 1:3 molar complex of hexazinone and urea in which hexazinone and urea are brought together in intimate contact on a molecular level by one of the following methods:

1. The hexazinone and urea can be dissolved in a common solvent and the hexazinone/urea complex isolated; the isolation from the common solvent can be by crystallization.
2. The hexazinone can be finely divided and contacted with an aqueous solution of urea in a fluid bed reactor, or other agitated bed device such as a "V" or double cone blender.

Another aspect of this invention relates to stable agricultural compositions which contain the hexazinone/urea complex of this invention as active ingredient and which can also contain an excess of free, i.e., uncomplexed hexazinone and free diuron in addition to the complex.

The complex exhibits the herbicidal activity of an equivalent amount of uncomplexed hexazinone and does not form low melting point eutectic mixtures with diuron.

DESCRIPTION OF THE INVENTION

Hexazinone and urea form a crystalline complex consisting of 1 mole of hexazinone and 3 moles of urea when the two compounds are brought together in intimate contact on a molecular level. This new complex possesses enhanced formulation properties when compared with the formulation properties of physical mixtures of hexazinone with diuron and also exhibits the herbicidal activity one would expect to obtain with the use of an equivalent amount of free, i.e., uncomplexed hexazinone.

The complex of the instant invention can be formed using any conventional techniques for achieving intimate contact between the hexazinone and urea which are known to those skilled in the art. For example, the complex can be crystallized from any solvent in which both hexazinone and urea are soluble, e.g., water, methanol or ethanol. Alternatively, the hexazinone/urea complex can be prepared by contacting finely divided hexazinone particles with an aqueous solution of urea in a fluid bed reactor or other agitated bed device such as a double cone blender.

The complex only forms between a 1:3 mole ratio of hexazinone and urea. If either of these materials is in excess of 1:3 mole ratio, the product obtained will normally consist of a mixture of the 1:3 mole complex and the ingredient that is in excess. As used herein, the term hexazinone/urea complex refers to the 1:3 molar complex of the two components.

The conclusion that the hexazinone/urea complex is a separate and distinct chemical entity rather than a mere physical mixture of hexazinone and urea is supported by analytical and physical evidence. For example, a difference is noted in the X-ray difraction pattern of the hexazinone/urea complex from either hexazinone or urea, thereby indicating that the hexazinone/urea complex has a new and different crystalline structure. The hexazinone/urea complex herein disclosed is a new chemical entity having a distinct melting point, a discrete crystalline habit and a different chemical structure than either unreacted hexazinone, unreacted urea or a physical mixture of the two materials.

The following examples are provided to further illustrate the hexazinone/urea complex, its method of preparation and enhanced formulation properties.

EXAMPLE 1

The following mixtures were prepared as 50 percent by weight total solid aqueous solutions at 50° C. They were then crystallized by cooling in an ice bath to 0° C., filtered and dried, and X-ray diffraction patterns were determined. Pattern A is the pattern for crystalline hexazinone; Pattern B is the pattern for crystalline urea; and Pattern C represents the crystalline hexazinone/urea complex.

Table 1

| | Solid Dissolved, Mol Ratio | |
|---|---|---|
| Mixture | Hexazinone | Urea |
| A | 1 | 1 |
| B | 1 | 2 |
| C | 1 | 3 |
| D | 1 | 4 |
| Mixture | weight percent Hexazinone | X-ray Diffraction of Crystalline Solids |
| A | 80.8 | Pattern A and C |
| B | 67.7 | Pattern A and C |
| C | 58.3 | Pattern C only |
| D | 51.2 | Pattern B and C |

Mixture C exhibited a single, unique X-ray diffraction pattern, which indicates the presence of a single compound or complex. When an aqueous solution of these crystals which contain 58.3 weight percent hexazinone is tested as an agricultural herbicidal spray, the biological activity is equivalent to that obtained by spraying an aqueous solution of the pure hexazinone at the same hexazinone concentration. The aqueous solution of mixture C crystals is extracted with methylene chloride in which urea is insoluble. All of the hexazinone is extracted forming a solution in methylene chloride while the urea remains in the aqueous phase. This indicates that the crystalline product is a complex and not a compound.

EXAMPLE 2

1.7 g of the crystalline product formed from mixture C in Example 1 were ground together with 2.4 g of diuron in a mortar and pestle to form a well mixed powder. 1.0 g of hexazinone and 2.4 g of diuron were mixed and ground similarly. A portion of each of the powders was placed in separate 13 mm Dia.×100 mm long culture tubes. The tubes were tightly stopped and immersed in boiling water for 10 minutes. After 10 minutes, the powder made using the hexazinone urea complex remained free flowing, but the powder made using uncomplexed hexazinone was a clear melt which solidified to a non-crystalline glass and remained tacky when left standing for several weeks at room temperature. The hexazinone urea complex remained stable, i.e., free-flowing, in contact with diuron.

The crystalline complex can be crystallized from any solvent in which both hexazinone and urea are soluble, for example, water, methanol or ethanol. Regardless of solvent used, the X-ray diffraction pattern C (Example 1) is exhibited by the crystalline material, i.e., the hexazinone/urea complex, which is recovered.

The hexazinone can be present both as the urea complex and as free hexazinone in stable formulations which contain diuron. When mixtures of urea and hexazinone which contain less urea than required to convert all the hexazinone to the complex are ground together in conventional processes, such as hammer milling or ball milling, the ground product exhibits an X-ray diffraction pattern which shows the presence of hexazinone as the major phase, hexazinone/urea complex and urea as minor phases. These mixtures containing at least 1 part by weight of urea to 5 parts by weight of hexazinone or 16.7 weight percent urea can be blended with diuron to prepare a formulation which contains total active ingredients as high as about 85 percent by weight with no reaction between the hexazinone and diuron. These formulations do not cake, and retain good water dispersibility after aging at elevated temperatures, i.e., up to about 45° C. It is postulated that the surface of the hexazinone particles is converted to the urea complex, and this surface layer is an effective barrier which prevents contact between free hexazinone and diuron. Thus, the low melting eutectic phase described above cannot form.

EXAMPLE 3

290 Parts by weight of hexazinone, 74 parts by weight of urea and 1 part by weight of fumed silica, (Cab-O-Sil M-5, Cabot Corporation, 125 High Street, Boston, Mass., 02110), were ground together in a ball mill for about 30 minutes until all of the ground material would pass a 100 mesh U.S. standard sieve ($\approx 150\mu$ sieve opening). The resulting powder, containing 80 percent by weight of total hexazinone, exhibited an X-ray diffraction pattern which indicated hexazinone as the major phase, and urea and hexazinone/urea complex as minor phases. The following mixtures were prepared by blending the above ground hexazinone containing powder with Karmex ® wettable powder herbicide containing 80 percent by weight of diuron (E. I. du Pont de Nemours and Co., Inc., Wilmington, Del. 19898):

Table II

| | Parts by weight of | | | |
|---|---|---|---|---|
| Mixture | Karmex ® | Hexazinone Powder | Tot. Active Wt. % | Weight Ratio Diuron: Hexazinone |
| 1 | 2 | 1.06 | 81.7 | 1:0.563 |
| 2 | 3 | 1.06 | 81.3 | 1:0.442 |
| 3 | 4 | 1.06 | 81.0 | 1:0.281 |
| 4 | 5 | 1.06 | 80.9 | 1:0.225 |
| 5 | 5.36 | 1.06 | 80.8 | 1:0.210 |

Each of the mixtures was exposed to a temperature of about 45° C. under a compressive load of 24 g/cm² (50 lb/ft²) in an air atmosphere for 21 days. After exposure, the mixtures were free-flowing powders with no evidence of caking or agglomeration observed. The aged mixtures dispersed rapidly and completely in water to form agglomerate-free sprayable suspensions.

EXAMPLE 4

100 g. of the Karmex ® wettable powder of Example 3 were blended with 64.3 g of the pulverized hexazinone/urea complex of Example 1 containing 58.3 weight percent of hexazinone, to prepare a mixture containing 71.5 weight percent of total active chemicals. The mixture did not cake or agglomerate when subjected to accelerated aging as in Example 3. The mixture remained a free-flowing powder and rapidly formed a uniform, agglomerate-free sprayable suspension in water.

The complex-coated hexazinone particles can be prepared also by contacting hexazinone particles with an aqueous solution of urea in a fluid bed reactor.

EXAMPLE 5

Batches of particulate hexazinone of particle size between about 74$\mu$ (200 mesh U.S. Standard Sieve) and 177$\mu$ (80 mesh U.S. Standard Sieve) were treated in a laboratory fluid bed reactor by spraying with aqueous solutions of urea and drying in the fluid bed as follows:

Table III

| | | Urea Solution | | | Calculated composition of recovered solids-wt. % | | |
|---|---|---|---|---|---|---|---|
| Batch | Hexazinone g. | Urea g. | Water g. | X-Ray Diffraction (Table II) | Complex | Hexazinone Free | Total |
| A | 90 | 10 | 15 | Pattern A + C | 24 | 76 | 90 |
| B | 85 | 15 | 15 | Pattern A + C | 36 | 64 | 85 |
| C | 80 | 20 | 17 | Pattern A + C | 48 | 52 | 80 |

X-ray diffraction patterns show no free urea present in the recovered solids indicating that all of the urea is present only as the complex.

EXAMPLE 6

Mixed herbicides were prepared by blending the treated hexazinone, batch C of Example 5, into commercial wettable powder herbicides as follows:

Table IV

| Hexazinone/ Urea complex wt. g. | Commercial Herbicide | |
|---|---|---|
| | Name | Wt. g. |
| 11.25 | Karmex ®, 80% Diuron[1] | 40 |
| 11.25 | Hyvar ®X, 80% Bromacil[1] | 40 |
| 11.25 | Krovar ®I, 80% Bromacil-diuron[1] | 30 |
| 11.25 | Sinbar ®, 80% Teracil[1] | |
| 11.25 | Aatrex ®, 80% Atrazine[2] | 40 |
| 11.25 | Evik ®, 80% Ametryne[2] | 40 |

[1] E. I. Du Pont de Nemours & Co., Wilmington, Delaware
[2] Ciba-Geigy, Greenville, S.C.

The herbicide mixtures were subjected to accelerated aging as in Example 3, and no evidence of caking was observed. All the mixtures formed excellent dispersions when mixed with water to form herbicidal spray slurries.

What is claimed is:
1. A hexazinone/urea complex in a molar ratio of 1:3.

* * * * *